US 8,821,510 B2

(12) United States Patent
Parker

(10) Patent No.: US 8,821,510 B2
(45) Date of Patent: Sep. 2, 2014

(54) FLEXIBLE SHEATH WITH POLYMER COIL

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1077 days.

(21) Appl. No.: 12/643,312

(22) Filed: Dec. 21, 2009

(65) Prior Publication Data
US 2010/0268243 A1    Oct. 21, 2010

Related U.S. Application Data

(60) Provisional application No. 61/169,590, filed on Apr. 15, 2009.

(51) Int. Cl.
*A61F 11/00* (2006.01)
*A61F 2/966* (2013.01)
*A61L 29/08* (2006.01)
*A61F 2/97* (2013.01)
*A61F 2/95* (2013.01)

(52) U.S. Cl.
CPC ............ *A61L 29/085* (2013.01); *A61F 2/966* (2013.01); *A61F 2002/9517* (2013.01); *A61F 2250/0039* (2013.01); *A61F 2002/9522* (2013.01); *A61F 2/97* (2013.01); *A61F 2/95* (2013.01)
USPC ........................................ 606/108

(58) Field of Classification Search
None
See application file for complete search history.

(56) References Cited

U.S. PATENT DOCUMENTS

| 5,069,674 A | 12/1991 | Fearnot et al. ............... 604/282 |
| 5,380,304 A | 1/1995 | Parker ........................ 604/282 |
| 5,695,483 A | 12/1997 | Samson ....................... 604/282 |
| 5,713,867 A * | 2/1998 | Morris ..................... 604/164.05 |
| 5,899,892 A | 5/1999 | Mortier et al. ............... 604/280 |

(Continued)

FOREIGN PATENT DOCUMENTS

| EP | 1 844 739 A1 | 10/2007 |
| WO | WO 94/10936 | 5/1994 |
| WO | WO 2004/030571 A2 | 4/2004 |
| WO | WO 2008/124844 A1 | 10/2008 |

OTHER PUBLICATIONS

International Search Report and Written Opinion, dated Nov. 24, 2010, pp. 1-11, PCT International Application No. PCT/US2010/030520, European Patent Office, The Netherlands.

*Primary Examiner* — Katherine Dowe
*Assistant Examiner* — Michael Mendoza
(74) *Attorney, Agent, or Firm* — Brinks Gilson & Lione

(57) ABSTRACT

A medical device including a tube having a coil fitted around at least a part of an inner liner, such as PTFE, and a braid extending over at least part of the coil. A polymeric layer is positioned over the braid to adhere to the inner liner. A portion of the coil advantageously comprises a polymer, such as PEEK, while the coil may also have a metal portion. The polymer coil may extend along at least at the proximal region of the tube, and the metal coil may extend along at least at the distal region of the tube. A polymer coil, a metal coil or any combination thereof can extend along the intermediate region of the tube. The polymer coil can be configured so that the tube is longitudinally splittable with a cutting instrument.

20 Claims, 3 Drawing Sheets

(56) References Cited

U.S. PATENT DOCUMENTS

| | | |
|---|---|---|
| 6,004,310 A | 12/1999 | Bardsley et al. ............... 604/524 |
| 6,171,295 B1 * | 1/2001 | Garabedian et al. .......... 604/524 |
| 6,497,681 B1 * | 12/2002 | Brenner ................... 604/164.05 |
| 6,709,429 B1 | 3/2004 | Schaefer et al. .............. 604/527 |
| 6,939,337 B2 * | 9/2005 | Parker et al. ................... 604/528 |
| 7,306,585 B2 | 12/2007 | Ross .............................. 604/523 |
| 7,527,606 B2 | 5/2009 | Oepen ...................... 604/103.04 |
| 2006/0200110 A1 | 9/2006 | Lentz et al. .................... 604/524 |
| 2007/0010867 A1 | 1/2007 | Carter et al. ................. 623/1.11 |
| 2007/0219617 A1 | 9/2007 | Saint ............................ 623/1.12 |
| 2007/0244540 A1 | 10/2007 | Pryor ........................... 623/1.11 |

* cited by examiner

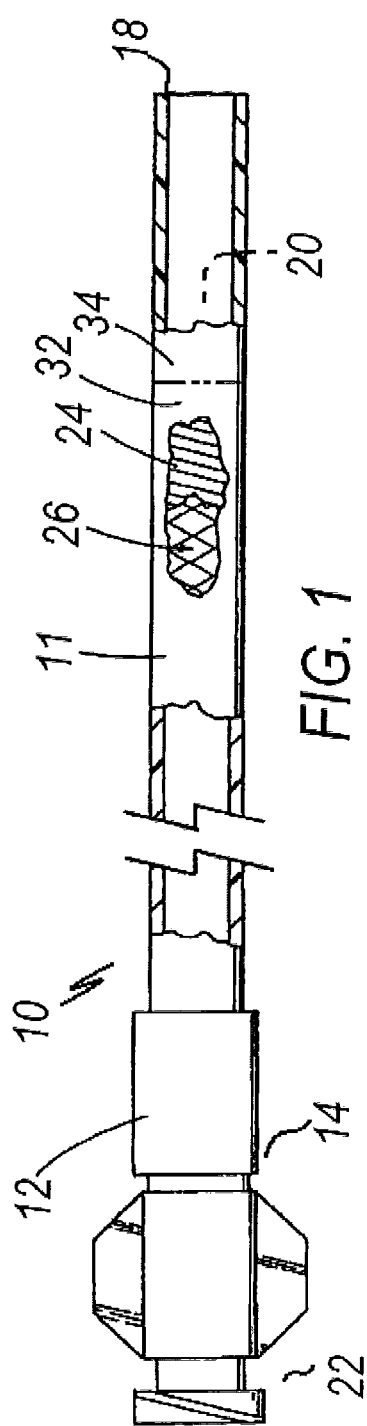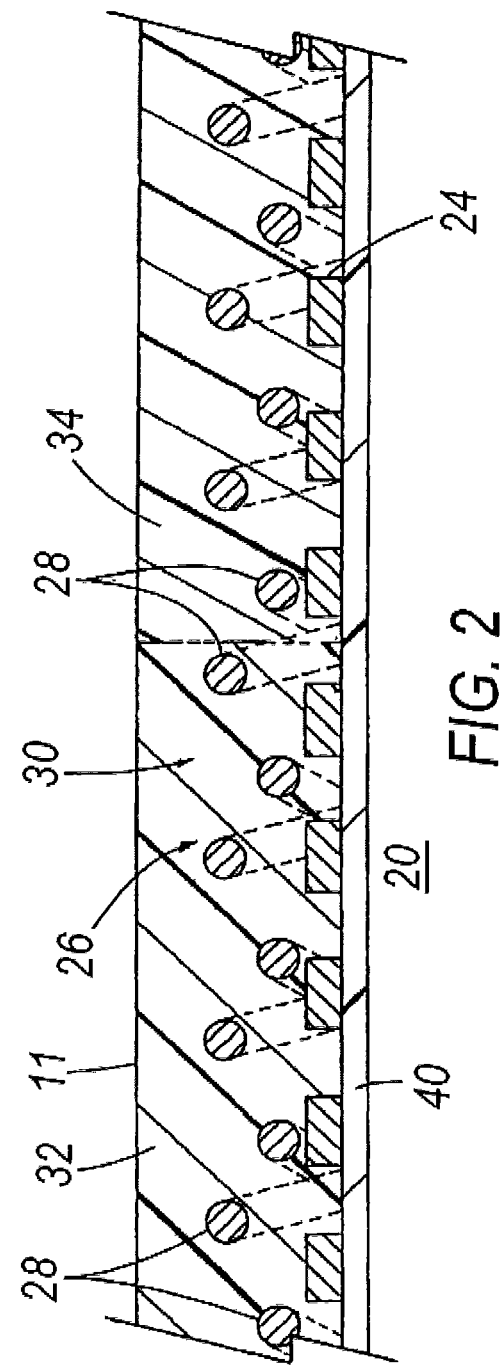

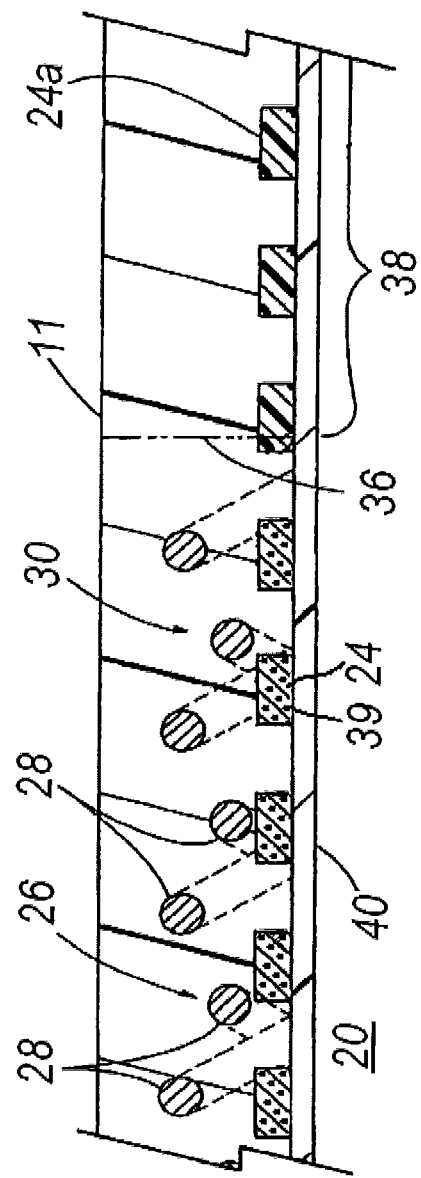
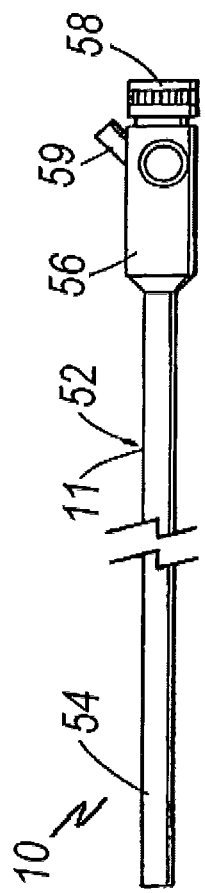
FIG. 3
FIG. 4

FLEXIBLE SHEATH WITH POLYMER COIL

CROSS-REFERENCE TO RELATED APPLICATIONS

This application is related to and claims priority and all benefits to U.S. Provisional Application Ser. No. 61/169,590 filed on Apr. 15, 2009, which is incorporated by reference in its entirety.

TECHNICAL FIELD

This invention relates generally to a medical device, and more particularly, to a tubular device for enhancing access to the vascular system of a patient.

BACKGROUND

Among the most important advances in modern medical practice has been the adoption of a variety of minimally invasive procedures. Examples of such minimally invasive procedures include angioplasty, endoscopy, laparoscopy, arthroscopy and the like. Minimally invasive surgical procedures such as these can be distinguished from conventional open surgical procedures. In these minimally invasive procedures, access to a target site within the body of a patient is achieved through a relatively small incision, into which a tubular device (including a tube of a device) is inserted or introduced. The tubular device maintains the patency of the incision, while permitting access to the target site via the interior (lumen) of the device.

The tubular device can be configured for surgical use itself, or can be incorporated into another device. One example of the former is a balloon catheter, wherein the tube is configured as a catheter shaft, and carries an inflatable balloon on the shaft. Balloon catheters are useful, e.g., for performing angioplasty and for the deployment of an expandable stent and/or graft for preventing stenosis (closure) of a body passage, such as a blood vessel. Other examples of the former include a diagnostic, infusion or drainage catheter, in which the tubular device is configured as a catheter for the delivery of a diagnostic or therapeutic fluid to the patient, or for the removal of a fluid from the patient. Examples of devices including apparatus in addition to the tube are endoscopes, laparoscopes, arthroscopes and the like, as well as guide catheters and introducer sheaths (percutaneous or otherwise), through which a guide wire or other surgical device may be introduced into the patient.

To enhance torqueability and pushability, some catheters have included a braided reinforcement in the wall of the catheter shaft. However, braided catheters are relatively susceptible to kinking during use. Once a catheter kinks, fluid cannot pass through the lumen of its shaft, and the catheter becomes essentially useless. In balloon catheters, this prevents inflation of the catheter balloon. In addition, in other catheters, such as diagnostic, infusion and drainage catheters, prevention of fluid flow similarly interferes with their satisfactory use. As a result, the initially introduced catheter must be removed, and another catheter must be introduced into the patient and once again advanced through the vascular system to the narrowed site. This wastes time and increases the potential for trauma to the patient. To prevent kinking, some catheters include a coil embedded in the wall of the catheter shaft, rather than a braid. Although the presence of a coil inhibits kinking of the catheter, catheters having an embedded coil are undesirably susceptible to necking, that is, an undesirable reduction in its outer and/or inner diameter. In addition, utilizing a coil instead of a braid does not provide a great a degree of torqueability.

U.S. Pat. No. 6,939,337, assigned to the assignee herein, discloses a tubular medical device that includes a coil, such as a flat wire coil, in a stressed radially expanded condition, and a braid that extends over at least part of the coil. A bonding layer, formed from a polymer such as nylon or polyurethane, is positioned over and contacts the coil, or both the coil and the braid. The polymeric bonding layer maintains the coil in the stressed radially expanded condition, and is bonded to an inner liner, such as PTFE. By providing both a coil and a braid, the tubular device achieves some advantages attainable from each of these reinforcements. For example, the coil enables the device to better resist collapse, necking and kinking during use. The braid provides the device with enhanced pushability, trackability and torqueability. The '337 patent is incorporated by reference herein in its entirety.

Although the device of the '337 patent represents an improvement over prior art devices, it is desired to make still further improvements to such tubular devices to enhance their utility to an even greater degree than presently available. For example, it may be advantageous to have a splittable catheter shaft wall to facilitate deployment of a tubular medical device within a body vessel. During complete deployment of a stent or graft, the physician must retract the sheath from the stent over its entire length. This can be difficult for longer stents, e.g., over 140 mm, especially self-expanding stents, as the force of retraction and length of retraction are greater, making it relatively cumbersome to retract and requiring both hands to overcome the friction force.

United States Patent Application Publication No. 2007/0244540A1 to Pryor, which describes a delivery system for delivery a self-expanding stent, provides one solution for this problem. The delivery system includes a sheath with a breakaway having less structural integrity than the remainder to the sheath such that the sheath preferentially splits at the breakaway upon contact with a keel. However, the specific construct of the sheath in Pryor's delivery system is not described, and incorporating a sheath with a breakaway having less structural integrity than the remainder to the sheath reduces trackability, pushability and torqueability, as well as increase the probability of necking or kinking along the breakaway, during use of the sheath.

Thus, it would be desirable to provide an arrangement of a coil and/or a braid in a tubular device possessing sufficient trackability, pushability and torqueability, as well as being highly resistant to collapse, necking or kinking, during use. It would also be desirable if the tubular device is capable of being split longitudinally along its wall.

SUMMARY OF THE INVENTION

The foregoing problems are solved and a technical advance is achieved in a medical device which comprises a tube having a highly uniform and repeatable inner and outer diameter, the tube possessing good trackability, pushability and torqueability, and the tube being highly resistant to collapse, necking or kinking during use.

In one embodiment, the tube includes a coil fitted around at least a part of an inner liner, such as PTFE, and a braid extending over at least part of the coil. A polymeric layer, typically a heat shrinkable material, is positioned over the braid and/or coil to adhere to the inner liner. While the polymeric layer has been described as being applied in tubular form over the coil, it can alternatively be extruded over and inside the coil to also form the inner liner. The polymeric layer can include at least two discrete longitudinal segments of differing durometer. This provides the resulting tube with differing stiffness at those segments, allowing selection of the flexibility of the tip of the tube. Selective flexibility of the tip of the tube can also be achieved by allowing the coil to extend distally beyond the braid.

The tube incorporated in the medical device advantageously has a portion of at least one of the coil and braid comprising a polymer. The polymer for the coil can be a high durometer polymer, such as PEEK. A polymer coil may further comprise reinforcing fibers, such as carbon fibers, for added strength and rigidity to the tube. In one example, a polymer coil extends throughout the entire tube. Yet, in other examples, the polymer coil extends at least along the proximal region of the tube. A metal coil can extend at least along the distal region of the tube. One advantage of having a metal coil along the distal region of the tube is enhanced crossability in comparison with a polymer coil. The braid can also be a polymer and/or a metal.

The tube can further extend from a handle having a cutting instrument to form a catheter. The tube is contactable with the cutting instrument in order for the cutting instrument to split the tube longitudinally. The distal region of the tube preferably has an axial length that is at least the axial length of a loadable tubular medical device. The proximal region of the tube preferably has an axial length that is at least the axial length of the loadable tubular medical device, and can be about 2 to 3 times the length depending on the application. A metal coil can also be placed adjacent the proximal region with the polymer coil so as to inhibit the cutting instrument from splitting the tube longitudinally. One advantage to having a polymer coil along the proximal region of the tube is the longitudinal splittability of the tube with a cutting instrument.

Exemplary devices which can incorporate the disclosed tube construction include, but are not limited to, balloon catheters (particularly, single lumen balloon catheters); stent deployment catheters, diagnostic, infusion and drainage catheters; endoscopes, laparoscopes and arthroscopes; guide catheters; and introducer sheaths.

Further objects, features, and advantages will become readily apparent to those skilled in the art after a review of the following detailed description of the preferred embodiments, with reference to the accompanying figures.

BRIEF DESCRIPTION OF THE DRAWINGS

FIG. 1 is a partially cross-sectional view of one embodiment of a medical device.

FIG. 2 is a cross-sectional view of a wall of a tube of the medical device illustrated in FIG. 1.

FIG. 3 is a cross-sectional view of a wall of a tube of another embodiment of a medical device.

FIG. 4 is a side elevation view of another embodiment of a medical device.

DETAILED DESCRIPTION OF THE DRAWINGS AND THE PRESENTLY PREFERRED EMBODIMENTS

Figure 5:
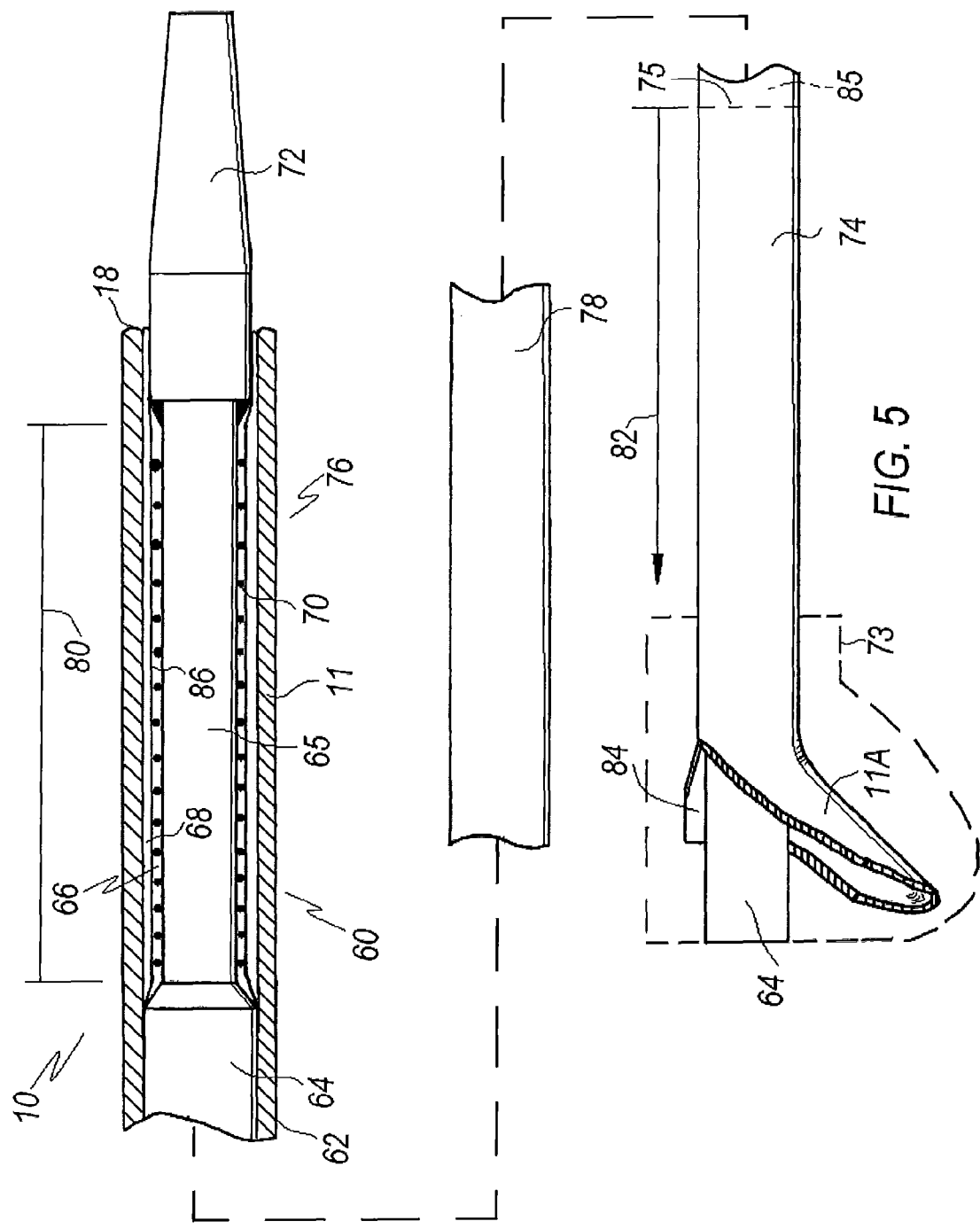
FIG. 5 is a partially cross-sectional view of another embodiment of a medical device.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the axial ends of the tubular medical device, as well as the axial ends of various component features. The "proximal" end is used in conventional manner to refer to the end of the tubular medical device (or component) that is closest to the operator during use of the assembly. The "distal" end is used in conventional manner to refer to the end of the tubular medical device (or component) that is initially inserted into the patient, or that is closest to the patient.

FIGS. 1 and 2 illustrate a first embodiment of a medical device 10 according to the present invention. Medical device 10 may comprise, for example, a guide catheter or an introducer sheath. Device 10 may also be useful for performing any of a variety of minimally invasive medical procedures, including, for example, angioplasty, diagnosis, chemotherapy, drainage, endoscopy, laparoscopy and arthroscopy.

Medical device 10 includes a main tube 11. Tube 11 includes a proximal end 14, a distal end 18, and a lumen 20 extending longitudinally therethrough. Tube 11 can extend in the distal direction from a conventional connector cap 22, as shown in FIG. 1. Tube 11 includes a coil 24, preferably formed of a ribbon comprising a medical grade polymer and/or a medical grade metal, such as stainless steel. The polymer of coil 24 can include a high durometer polymer (durometer type D), such as polyether ether ketone (PEEK) with a durometer of about D85 or other polymers having similar desired properties, as well as aramid fiber materials (e.g., KEVLAR) with a durometer of about D70. The polymer PEEK has been found to have excellent mechanical properties and machinability. Tube 11 also includes a braid 26 extending over at least part of coil 24. Braid 26 preferably comprises a plurality of crossed wires 28 of circular or flat cross-section, and is preferably comprised of a medical grade metal such as stainless steel, or medical grade polymer such as aramid fiber materials (e.g., KEVLAR). Other medical grade materials may also be useful for the coil and the braid.

Tube 11 further includes a polymeric bonding layer 30 positioned over and contacting at least coil 24, and preferably contacting braid 26 as well, in order to adhere to the coil and/or the inner liner. More preferably, polymeric layer 30 comprises heat-shrinkable (heat fused) tubing, such as a polyether block amide, polyamide (nylon), PTFE, and/or polyurethane. During manufacture, a sleeve of FEP heat-shrinkable tubing (heat fused shrink tubing) may be utilized that is stripped after manufacture.

Any particular portion of tube 11 can be given a flexibility or springiness which is different from the flexibility or springiness of the remainder of the tube. There are several ways in which this difference can be achieved. One way would be to vary the thickness of polymeric layer 30 along the length of tube 11; this may not be a particularly practical way to achieve the desired difference. Another way is to permit polymeric layer 30 to comprise at least two discrete longitudinal segments (such as proximal segment 32 and distal segment 34) of differing durometer. Making the distal segment 34 of polymeric layer 30 from a softer material than that from which the proximal segment 32 is made yields a tube 11 with a tip that is more flexible or springier than the balance of the tube. Alternatively, as shown in FIG. 3, the coil, shown as a metal coil 24A, may extend distally beyond a distal end 36 of braid 26. This leaves a distal portion 38 of coil 24 which is not covered by the braid 26, and similarly yields a tube 11 whose tip is more flexible or springier than the balance of the tube. Preferably, coil 24 comprises a metal coil substantially along a large portion of its length to inhibit necking and improve kink resistance.

Also shown in FIG. 3, coil 24 can be a composite fabricated at least in part using a polymer, such as PEEK, which may be combined with reinforcing fibers 39, e.g., carbon fiber or glass fiber, with the reinforcing material being added to the PEEK matrix in order to reinforce the composite ribbon coil for added strength and rigidity. When presented, fibers 39 preferably are disposed longitudinally parallel to the sides of the coil ribbon to improve the strength of the coil.

Tube 11 optionally can further include an inner liner 40 beneath and in contact with at least part of coil 24. Inner liner 40 is made of a medical grade polymer, and may have a melt temperature greater than the melt temperature of polymeric layer 30. Inner liner 40 preferably comprises a lubricious polymer, such as PTFE. Lumen 20 can be sized depending on the application, e.g., sized to receive a conventional guide wire (not shown) or a tubular medical device (FIG. 5) therein, or the lumen can be intended for the delivery of a diagnostic or therapeutic fluid, or the removal of a fluid from the patient.

Coil 24 permits medical device 10 to have a wall which is thinner than might conventionally be achieved, and gives medical device 10 more flexibility and springiness. During use, tube 11 of medical device 10 provides a sufficient stiffness for straightening in order to make medical device 10 easier to control during advancement of the medical device in the patient. Coil 24 also provides significant advantages during the manufacture of the medical device 10, most notably, better control over the wall thickness ultimately possessed by the medical device.

Construction of tube 11 of the present invention can be straightforward. A mandrel is selected which has a diameter at least the size of the unstressed, free inner diameter of coil 24. If employed, inner liner 40 is placed on the mandrel. Coil 24 is then fitted or wrapped about the mandrel (and inner liner 20, if present), the mandrel temporarily maintaining coil 24 in an expanded condition with a diameter larger than the unstressed, free inner diameter. Coil 24 can be compression fitted or radially expanded attached, even stressed, radially expanded during manufacture. Stress, radially expanded fitting is described in U.S. Pat. No. 6,939,337 to Parker et al., which was previously incorporated. The coil and the inner liner may be chemically etched or roughened for improved adhesion. Braid 26 is then positioned over coil 24. Finally, polymeric layer 30 is established over braid 26 and coil 24. As indicated above, polymeric layer 30 is preferably formed from a heat-shrinkable tubing. The mandrel and the elements thereon are heated to shrink and cure polymeric layer 30 to cause it to thermally bond to coil 24 and/or bond to inner liner 40. (The spacing of braid 26 must be chosen, of course, to allow such bonding or other adhesion to occur.) The mandrel and formed tube 11 are then cooled and the heat reduced sleeve removed, and the tube is removed from the mandrel. Polymer and/or metal coil can be wound by positioning the mandrel and the inner liner the head and tail sock of a lathe. A coil transfer mechanism is mounted on the lathe carriage. The mandrel and inner liner are rotated and the coil is wrapped thereon, as the coil transfer mechanism moves longitudinally parallel to the mandrel. More details for applying a coil to form a tube can be found in U.S. Pat. No. 5,380,304 to Parker, which is incorporated by reference in its entirety. Optionally, the coil can be manually applied around the mandrel. For a polymer coil, in particular, it has been found better to attach the initial end of the coil to the inner liner by applying an adhesive, such as LOCTITE, to the end before winding the coil, and when finished similarly attaching the second end of the coil. Heat from a heat gun can also be applied to the coil before and/or after the winding to relax the coil before application of the polymeric layer.

Tube 11 can be put to use in medical devices other than simple catheters. For example, as shown in FIG. 4 medical device 10 can instead be an endoscope 52 of otherwise conventional construction, save for the inclusion of tube 11. In such a case, tube 11 is configured as an endoscope sheath 54 connected to a conventional endoscope handle 56, the handle 56 including an ocular tube 58 and a forceps insertion inlet (sidearm) 59.

Alternatively, medical device 10 can instead be a single lumen catheter 60 of otherwise conventional construction, again save for the inclusion of tube 11. In this case, tube 11 is configured as a catheter shaft 62, and medical device 10 then further comprises an inner catheter 64 extending through the tube lumen 20. A distal portion 65 of inner catheter 64 can have a reduced cross-sectional area such that a stent retaining region 66 is defined in an annular space 68 created between catheter shaft tube 62 and inner catheter 64. Annular space 68 is dimensioned to receive a loaded tubular medical device 70, such as a stent and/or graft, which is disposed around within the stent retaining region 66 in a pre-delivery configuration. Tubular medical device 70 can be expandable to an expanded configuration by mechanical means such as a balloon catheter as known in the art or is preferably self-expandable as known in the art. A distal tip 72 can be attached to the distal end of inner catheter 64 to facilitate dilation of the body vessel during navigation therethrough. A handle 73 attached at the proximal end of catheter 60 is shown in a dashed line to represent any shape and configuration desirable for its application.

Tube 11 may have multiple longitudinal regions having coil 24, braid 26, or various combinations thereof disposed along each of the regions. For example, in FIG. 5 tube 11 includes a proximal region 74, a distal region 76, and an intermediate region 78 therebetween. Coil 24 preferably extends over at least a portion of each of the proximal, intermediate, and distal regions of the tube. Distal region 76 of the tube has an axial length 80 generally from the distal end 18 of the tube 11 (shown just short of distal end 18) that is at least the axial length of stent retaining region 66 that is sized for tubular medical device 70. Proximal region 74 of the tube has an axial length 82 generally from the proximal end 14 of the tube 11 to a position more distal which is shown as a dashed line 75. Axial length 82 is sized to be at least the axial length of tubular medical device 70 in order to permit retraction of the outer catheter from the loaded medical device, and can be about 2 to 3 times the length of tubular medical device 70 depending on the application.

In one example, a polymer coil extends throughout the tube. In another example, a polymer coil extends at least along proximal region 74 of the tube and a metal coil extends at least along distal region 76 of the tube. A polymer coil, a metal coil or any combination thereof can extend along intermediate region 78 of the tube. It may be advantageous to incorporate a metal coil along distal region 76 of tube 11, instead of a polymer coil, to improve crossability of the tube through the body vessel. Crossability refers to the ability to navigate a catheter across narrow restrictions in the vasculature, such as stenosed vessels or fully and partially deployed stents. A metal coil along distal region 76 of tube 11 may also improve the column strength of the tube in order to better withstand the radially expansive forces of a self-expanding tubular medical device loaded within the tube lumen. One example of an illustrated preferred distal region is in FIG. 3, where distal portion 38 of coil 24 is not covered by braid 26 and comprises the metal coil 24A, and coil 24 comprises a polymer coil, with or without the reinforcing fibers 39, adjacent distal portion 38.

In a preferred embodiment of a medical device 10, a polymer coil and braid (not shown) extend along proximal region 74 of tube 11 and a cutting instrument 84, such as a scalpel blade, is suitably positioned within handle 73 to split the wall of tube 11 longitudinally when contacted therewith. Cutting instrument 84 is dimensioned, as well as having a sharpness, to slice through the inner liner, the polymer coil (with or without reinforcement fibers), the braid (polymer or metal) and the polymer layer of the tube. After splitting, a split tube portion 11A is formed and can be wound about a spool (not shown) within handle 73 to confine the split tube in a small space or simply be pulled out of the handle away from the slicing point. Instead of having to retract longitudinally a portion of the handle attached to the catheter shaft tube the length of the tubular medical device to deploy tubular medical device 70 as conventionally performed, which can be cumbersome and difficult for longer devices in tight operating environments, the physician need only control and contain the split tube portion that is typically through use of the handle.

In one example, tube 11 can include a metal coil segment 85, shown beginning at a dashed line 75 to indicate its location within the tube wall, disposed adjacent proximal region 74 to define a maximum splitting region of tube 11. Blade 84 can slice tube 11 distally for the length of proximal region 74 as catheter shaft tube 62 is being retracted for stent deployment. However, metal coil 85, defining the end of the proximal region, functions as a physical stop as the blade is not adapted to cut through the metal coil, thereby providing the physician tactile feedback, indicating the deployment of tubular medical device 70 from the catheter.

According to FIG. 5, catheter 60 can further comprise an everting deployment catheter having a rolling liner 86 attached between catheter shaft tube 62 and inner catheter 64. With relative axial movement between catheter shaft tube 62 and inner catheter 64, rolling liner 86 can be everted between a fully extended or unrolled position and a fully everted or folded position that is shown in FIG. 5. Rolling liner 86 preferably is formed of a tube comprising a medical grade polymer that is lubricious, such as PTFE. The rolling liner can be an extension of inner liner 40 such that only one tube is used for both. In this instance, the distal end of the rolling liner is everted and circumferentially attached to the exterior surface of inner catheter 64 by an adhesive. Rolling liner 86 is shown disposed in annular space 68 around distal portion 65 of the inner catheter, to retain tubular medical device 70 in the pre-delivery loaded configuration. Retraction of catheter shaft tube 62 relative to inner catheter 64 peels or unrolls a contacting portion of rolling liner 86 from tubular medical device 70, thereby allowing the tubular medical device to expand. Since the rolling liner is everted upon itself, retraction lengths of catheter shaft tube 62 is longer, typically being at least twice the length of the tubular medical device. This can be problematic for longer stents; e.g., the retraction length would be at least 400 mm for a 200 mm length stent. Thus, a reinforced tube as described herein is capable of being split longitudinally, especially with blade 84, which is particularly useful for everting deployment systems.

The dimensions (for example, the thickness) of the various elements mentioned above should be selected in view of the purpose of medical device 10 in which tube 11 is incorporated. It is believed that the selection of such dimensions will lie within the level of skill in the art of designing surgical instruments, once benefit of the present disclosure is had. While a modest amount of trial-and-error may be needed to obtain optimal dimensions, it is believed that any required experimentation will not be undue. The following may constitute the thicknesses of the various elements of a typical embodiment of tube 11: inner liner 20, about 0.0015 in. (about 0.038 mm) thick; ribbon of coil 24, about 0.0008 to about 0.001 in. (about 0.020 to 0.025 mm) thick; wires 28 of braid 26, about 0.001 in. (about 0.025 mm) in diameter; and polymeric layer 18, about 0.045 in. (about 1.14 mm) thick.

The medical device 10 is particularly useful for the performance of a wide variety of catheterization procedures. A medical device 10 including tube 11 can be configured as a balloon catheter (particularly, a single lumen balloon catheter); a diagnostic, infusion or drainage catheter; an endoscope, laparoscope, arthroscope or the like; a guide catheter; or an introducer sheath, among other devices. The present invention is particularly advantageous over prior medical devices in that tube 11 is highly resistant to collapse, necking and kinking during use and possesses good trackability, pushability and torqueability during use. Tube 11 can possess a polymer coil that is splittable with a blade so that the body of the split tube can be manipulated such as being wound about a spool in order to eliminate the retraction length typically required with handles. To this end, during deployment of a stent or graft, especially longer stents, e.g., over 140 mm, the physician can retract the catheter tube from the stent over its entire length with relative ease and in a more compact environment, making it less cumbersome for the physician. Moreover, the present invention enjoys significant advantages during manufacture, having a highly uniform and repeatable inner and outer diameter.

The details of the construction or composition of the various elements of medical device 10 not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure. For practical reasons, however, most embodiments of medical device 10 should probably be considered to be single-use devices, rather than being reusable.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:

1. A medical device comprising a tube, wherein the tube comprises:
   an inner liner defining a lumen extending longitudinally through the tube;
   a coil fitted around at least a part of the inner liner;
   a braid extending over at least part of the coil, wherein a portion of the coil comprises a polymer; and a polymeric layer positioned over the braid to adhere to the inner liner,
wherein a portion of the coil disposed along a first longitudinal region of the tube comprises a polymer, and the first longitudinal region is free from a metal portion of the coil, and another portion of the coil disposed along a second longitudinal region comprises a metal, and the second longitudinal region is free from a polymer portion of the coil.

2. The medical device according to claim 1, wherein the polymeric layer is thermally bonded to the inner liner.

3. The medical device according to claim 1, wherein the inner liner comprises polytetrafluoroethylene (PTFE).

4. The medical device according to claim 1, wherein the polymer coil portion comprises a high durometer material.

5. The medical device according to claim 4, wherein the high durometer material comprises PEEK.

6. The medical device according to claim 4, wherein the high durometer material is a durometer type D material.

7. The medical device according to claim 1, wherein the polymer coil portion further comprises reinforcement fibers.

8. The medical device according to claim 1, wherein a portion of the braid comprises a polymer.

9. The medical device according to claim 1, wherein the braid comprises a metal.

10. The medical device according to claim 1, wherein the polymeric layer comprises at least one of polyamide, a polyether block amide, polyurethane and polytetrafluoroethylene (PTFE).

11. The medical device according to claim 1, wherein the polymeric layer comprises at least two discrete longitudinal segments of differing durometer.

12. The medical device according to claim 1, wherein the coil is a flat wire coil.

13. A medical device comprising a tube including a proximal region, a distal region, and an intermediate region therebetween, wherein the tube comprises: an inner liner defining a lumen extending longitudinally through the tube, a polymeric layer positioned over the inner liner to adhere to the inner liner, and a coil and a braid adhered between the inner liner and the polymeric layer, wherein the coil extends along at least a portion of each of the proximal, intermediate, and distal regions of the tube, and the braid extends along at least a portion of each of the proximal and intermediate regions of the tube, wherein a portion of the coil comprises a polymer along at least the proximal region of the tube and the proximal region is free from a metal portion of the coil, and the coil comprises a metal at least along the distal region of the tube and the distal region is free from a polymer portion of the coil.

14. The medical device according to claim 13, wherein the coil comprises a polymer along the proximal region of the tube, and the proximal region is free from a metal portion of the coil.

15. The medical device according to claim 13, wherein the coil is a flat wire coil.

16. A catheter for introduction of a tubular medical device to a body vessel, the catheter comprising: a handle having a cutting instrument; and a tube extending from the handle, having a proximal region, a distal region, and an intermediate region therebetween, the tube comprising an inner liner defining a lumen extending longitudinally through the tube, a coil fitted around at least a part of the inner liner, a braid extending over at least part of the coil, wherein a portion of the coil comprises a polymer, and a polymeric layer positioned over the braid to adhere to the inner liner, wherein the tube is contactable with the cutting instrument of the handle in order to split at least a portion of the tube longitudinally, and wherein the coil comprises a polymer along the proximal region of the tube with the proximal region being free from a metal coil portion, and a metal coil distally adjacent the polymer coil along the proximal region of the tube to inhibit the cutting instrument of the handle from splitting the tube longitudinally.

17. The catheter according to claim 16, wherein the distal region of the tube has an axial length defined to be at least a length of a tubular medical device to be loaded within the tube lumen.

18. The catheter according to claim 16, wherein the proximal region of the tube has an axial length defined to be at least a length of a tubular medical device to be loaded within the tube lumen.

19. The catheter according to claim 18, wherein the coil is a flat wire coil.

20. The catheter according to claim 19, wherein a thicknesses of the coil 24 is about 0.0008 to about 0.001 in.

* * * * *